United States Patent [19]

Heintze

[11] 4,123,511

[45] Oct. 31, 1978

[54] THERAPEUTIC COPPER COMPOSITIONS

[75] Inventor: York Heintze, Bochum, Fed. Rep. of Germany

[73] Assignee: Gertrude Fischer, East Liverpool, Ohio

[21] Appl. No.: 592,463

[22] Filed: Jul. 2, 1975

Related U.S. Application Data

[63] Continuation of Ser. No. 487,713, Jul. 11, 1974, abandoned.

[51] Int. Cl.$^2$ .......................... A61K 9/14; A61L 9/04; A61K 33/34; A61K 31/695
[52] U.S. Cl. ........................................ 424/46; 424/45; 424/141; 424/184; 424/195; 424/294; 424/343; 424/350
[58] Field of Search .................. 424/45, 46, 140, 141, 424/DIG. 13, 294, 195, 343, 350

[56] References Cited

FOREIGN PATENT DOCUMENTS 987,301  3/1965  United Kingdom ...................... 424/46

OTHER PUBLICATIONS

*Handbook of Therapy*, (1937), 11th Ed., p. 30, Amer., Med. Assoc., Chicago.
*The Extra Pharmacopoeia*, (1958), 24th Ed., pp. 450-451 & 1366-1367, The Pharmaceutical Press-London.
*The Merck Index*, (1960), 7th Ed., p. 750, Merch & Co., Inc., Rahway, N.J. U.S.A.
*The Pharmaceutical Journal*, 24 Oct. 1964, pp. 396-401.

Primary Examiner—Frederick E. Waddell
Attorney, Agent, or Firm—Jacobs & Jacobs

[57] ABSTRACT

Therapeutic copper compositions are described which are adapted to be applied as from an aerosol container to areas of human skin for the treatment of muscle spasms and cramps, mild burns and insect bites and to enhance healing by increasing blood circulation beneath the skin and to normalize the pH of the skin area being treated. The copper is in the form of a copper powder or copper oleate.

7 Claims, No Drawings

THERAPEUTIC COPPER COMPOSITIONS

CROSS-REFERENCE

This is a continuation of Ser. No. 487,713 filed July 11, 1974, now abandoned.

The present invention relates to copper-containing compositions for external application to human skin to stimulate and increase circulation of blood beneath the skin, to enhance healing of mild burns and insect bites and to overcome muscular spasms and cramps. The compositions also have antifungal action against fungal infections such as athlete's foot.

The compositions of the invention are in either of two forms suitable for filling into aerosol containers under pressure with a propellant, one of which is termed a copper spray and the other of which is termed a colorless spray. The copper spray is made up of copper powder, 98% of which is 300 mesh, colloidal silica such as silica aerogel and oil of rosemary in isopropyl or ethyl alcohol and methylene chloride. The propellant is $CO_2$ or preferably a 50:50 or 30:70 mixture of Freon 11 which is trichlorofluoromethane and Freon 12 which is dichlorodifluoromethane.

The colorless spray differs primarily from the copper spray in the use of copper oleate (10%). Copper oleate is per se known and is defined as a mixture of 10% copper oxide dissolved in oleic acid and forming a greenish-blue, granular powder soluble in ether.

The copper powder in the copper spray is used in the range of about 2–10% of the composition whereas the copper oleate (10%) in the colorless spray is used in the range of 0.30–0.75%. The colloidal silica, e.g. silica aerogel, is used in the range of 0.40–0.60% and the oil of rosemary is used in the amount of about 5%. All percentages are by weight of the compositions. The isopropyl or ethyl alcohol and the methylene chloride are used in amounts sufficient to obtain a suitable suspension in the case of the copper spray or a solution in the case of the colorless spray. The proportions are set forth in the following examples, it being understood that other suitable propellants may be substituted for the Freon 11 and Freon 12 which are preferred. The invention is illustrated by the following examples:

EXAMPLE 1

| Copper Powder | 5.00% |
|---|---|
| Copper Oleate | — |
| Silica Aerogel | 0.53% |
| Oil of Rosemary | 5.00% |
| Isopropyl Alcohol | 29.71% |
| Methylene Chloride | 12.70% |
| Freon 11 | 14.12% |
| Freon 12 | 32.94% |
| | 100.00% |

EXAMPLE 2

| Copper Powder | — |
|---|---|
| Copper Oleate | 0.53% |
| Silica Aerogel | 0.41% |
| Oil of Rosemary | 5.00% |
| Isopropyl Alcohol | 34.35% |
| Methylene Chloride | 12.65% |
| Freon 11 | 14.12% |
| Freon 12 | 32.94% |
| | 100.00% |

The compositions of the invention when sprayed upon affected human skin areas leave a temporary brownish coloration which is useful in delimiting the area to which the composition is applied. The brownish coloration is, however, non-staining and is readily removable by water or by washing. It is normally left on the skin until the purpose of the conposition is accomplished. This ordinarily requires only a few minutes although no adverse side effects have been found up to several hours. When the compositions are applied to the skin, there is a feeling of warmth accompanied by increased circulation of blood and this has been found to be beneficial in the treatment of muscular cramps or spasms so that the compositions exert anti-spasmodic activity. The compositions also appear to have astringent action although the general effect is soothing and emollient. When applied over mild burns or insect bites, it gives almost immediate relief. The compositions also are active against some fungi particularly the fungus of athlete's foot. Measurements of skin pH show that the pH value is normalized. The compositions are non-toxic and non-injurious and have not been found to cause any adverse side effects. The compositions may be used as frequently as needed.

The combination of copper or a copper-containing material with silica aerogel and oil of rosemary have a potentiating action since the therapeutic action of the compositions cannot be obtained from the individual components employed separately or consecutively. The function of the colloidal silica is as a dispersing agent to keep the composition uniform and homogeneous, and while the proportion of ingredients may be somewhat varied, it will be understood that they are used in such amounts and proportions as will enable them to be readily expelled from aerosol containers into which they have been filled under pressure with a propellant and without clogging the usual aerosol container valve.

The typical aerosol container has 100 grams of composition under pressure therein of which about 53 grams is a composition according to the present invention and about 47 grams is freon or other suitable propellant. No special procedure is required for mixing the compositions and filling them into aerosol containers, but it has been found best in the case of the powder copper composition to mix the same with the colloidal silica, to add the same to the alcohol solvent and dispersing agent and then to add the oil of rosemary which is of Spanish origin and of U.S. pharmacopoeia quality. The methylene chloride is then added to the entire composition, mixed and then filled into aerosol containers under pressure with a propellant in a manner per se known. In using copper oleate instead of copper powder, the copper oleate is preferably dissolved in warmed isopropyl alcohol and then the foregoing procedure followed. The composition using copper powder is a suspension whereas the copper oleate composition is a solution.

What is claimed is:

1. A non-staining, water-removable sprayable therapeutic copper-containing composition having anti-spasmodic and fungicidal activity for external application to human skin for the treatment of muscle spasms and cramps and athlete's foot fungus which composition consists essentially of a therapeutically potentiating combination of about 2–10% of the composition of a suspension of metallic copper powder or about 0.25–0.75% of the composition of a solution of copper oleate, about 0.4–0.6% of the composition of colloidal silica and about 5% oil of rosemary in isopropyl or ethyl alcohol and methylene chloride, said percentages being by weight.

2. A composition of claim 1 wherein the copper powder is 98% 300 mesh.

3. A composition of claim 1 wherein the copper powder amounts to about 5% of the composition.

4. A composition of claim 1 wherein the copper oleate amount to about 0.50% pf the composition.

5. A composition of claim 1 wherein the colloidal silica is silica aerogel.

6. A composition of claim 1 filled into a valved aerosol container with a fluorocarbon or mixture of fluorocarbons as propellant under pressure.

7. A composition of claim 1 filled into a valved aerosol container with a $CO_2$ propellant under pressure.

* * * * *